United States Patent
Haggstrom et al.

(10) Patent No.: US 10,463,773 B2
(45) Date of Patent: Nov. 5, 2019

(54) WOUND DRESSING WITH VACUUM RESERVOIR

(71) Applicant: Smith & Nephew Inc., Memphis, TN (US)

(72) Inventors: Kurt Haggstrom, Huntington Beach, CA (US); E. David Fink, Franklin, MA (US); Katja Grundmeier, London (GB)

(73) Assignee: Smith & Nephew, Inc., Memphis, TN (US)

( * ) Notice: Subject to any disclaimer, the term of this patent is extended or adjusted under 35 U.S.C. 154(b) by 429 days.

(21) Appl. No.: 15/280,009

(22) Filed: Sep. 29, 2016

(65) Prior Publication Data

US 2017/0014556 A1 Jan. 19, 2017

Related U.S. Application Data

(60) Continuation of application No. 14/585,589, filed on Dec. 30, 2014, now Pat. No. 9,456,928, which is a
(Continued)

(51) Int. Cl.
*A61F 13/00* (2006.01)
*A61M 1/00* (2006.01)
(Continued)

(52) U.S. Cl.
CPC ..... *A61M 1/0027* (2014.02); *A61F 13/00063* (2013.01); *A61F 13/00068* (2013.01);
(Continued)

(58) Field of Classification Search
CPC .......... A61F 13/00055; A61F 13/00059; A61F 13/00068; A61F 13/0209; A61F 13/0216;
(Continued)

(56) References Cited

U.S. PATENT DOCUMENTS 3,874,387 A 4/1975 Barbieri
3,972,328 A 8/1976 Chen
(Continued)

FOREIGN PATENT DOCUMENTS

DE 198 44 355 4/2000
DE 20 2004 017 052 6/2005
(Continued)

OTHER PUBLICATIONS

Kendall ULTEC Hydrocolloid Dressing (4"x×"), product ordering page, web page downloaded Jul. 13, 2014.
(Continued)

*Primary Examiner* — Catharine L Anderson
(74) *Attorney, Agent, or Firm* — Knobbe, Martens, Olson & Bear LLP

(57) ABSTRACT

A wound dressing apparatus includes a wound dressing member dimensioned for positioning relative to a wound bed. The wound dressing member including an internal vacuum reservoir and has a port in communication with the vacuum reservoir for applying subatmospheric pressure to the vacuum reservoir to facilitate removal of fluid from the wound bed. The wound dressing member includes a visual pressure indicator associated therewith for indicating a level of pressure within the vacuum reservoir. The visual pressure indicator includes color indicia having a plurality of colors corresponding to a condition of the pressure within the vacuum reservoir. The wound dressing member includes a lower absorbent member positionable adjacent the wound bed and an upper member which at least partially defines the vacuum reservoir. At least one of the top member and the lower absorbent member has the visual pressure indicator mounted thereto.

19 Claims, 11 Drawing Sheets

Related U.S. Application Data continuation of application No. 13/775,964, filed on Feb. 25, 2013, now Pat. No. 8,956,336, which is a continuation of application No. 12/686,813, filed on Jan. 13, 2010, now Pat. No. 8,409,157, which is a division of application No. 11/516,925, filed on Sep. 6, 2006, now Pat. No. 7,699,823.

(60) Provisional application No. 60/714,805, filed on Sep. 7, 2005.

(51) Int. Cl.
*A61F 13/02* (2006.01)
*A61M 39/24* (2006.01)
*A61M 27/00* (2006.01)

(52) U.S. Cl.
CPC ...... *A61F 13/0209* (2013.01); *A61F 13/0216* (2013.01); *A61M 1/0031* (2013.01); *A61M 1/0088* (2013.01); *A61M 39/24* (2013.01); *A61M 27/00* (2013.01); *A61M 2205/15* (2013.01); *A61M 2205/18* (2013.01); *A61M 2205/3344* (2013.01); *A61M 2205/3368* (2013.01); *A61M 2205/583* (2013.01); *A61M 2205/584* (2013.01); *A61M 2205/587* (2013.01); *A61M 2205/6081* (2013.01); *A61M 2205/8206* (2013.01)

(58) Field of Classification Search
CPC .............. A61M 1/0025; A61M 1/0027; A61M 1/0029; A61M 1/0031; A61M 1/0088; A61M 2205/15; A61M 2205/18; A61M 2205/3344; A61M 2205/583; A61M 2205/584; A61M 2205/587
See application file for complete search history.

(56) References Cited

U.S. PATENT DOCUMENTS

| | | |
|---|---|---|
| 4,224,941 A | 9/1980 | Stivala |
| 4,398,910 A | 8/1983 | Blake et al. |
| 4,624,656 A | 11/1986 | Clark et al. |
| 4,655,754 A | 4/1987 | Richmond et al. |
| 4,681,562 A | 7/1987 | Beck et al. |
| 4,710,165 A | 12/1987 | McNeil et al. |
| 4,826,494 A | 5/1989 | Richmond et al. |
| 4,969,880 A | 11/1990 | Zamierowski |
| 5,055,195 A | 10/1991 | Trasch et al. |
| 5,055,198 A | 10/1991 | Shettigar |
| 5,056,510 A | 10/1991 | Gilman |
| 5,100,396 A | 3/1992 | Zamierowski |
| 5,106,629 A | 4/1992 | Cartmell et al. |
| 5,141,503 A | 8/1992 | Sewell, Jr. |
| 5,152,757 A | 10/1992 | Eriksson |
| 5,176,663 A | 1/1993 | Svedman et al. |
| 5,181,905 A | 1/1993 | Flam |
| 5,234,419 A | 8/1993 | Bryant et al. |
| 5,238,732 A | 8/1993 | Krishnan |
| 5,261,893 A | 11/1993 | Zamierowski |
| 5,527,293 A | 6/1996 | Zamierowski |
| 5,549,584 A | 8/1996 | Gross |
| 5,562,107 A | 10/1996 | Lavender et al. |
| 5,636,643 A | 6/1997 | Argenta et al. |
| 5,643,189 A | 7/1997 | Masini |
| 5,645,081 A | 7/1997 | Argenta et al. |
| 5,678,564 A | 10/1997 | Lawrence et al. |
| 5,701,917 A | 12/1997 | Khouri |
| 5,707,499 A | 1/1998 | Joshi et al. |
| 5,759,570 A | 6/1998 | Arnold |
| 5,779,657 A | 7/1998 | Daneshvar |
| 5,833,646 A | 11/1998 | Masini |
| 5,911,222 A | 6/1999 | Lawrence et al. |
| 6,071,267 A | 6/2000 | Zamierowski |
| 6,117,111 A | 9/2000 | Fleischmann |
| 6,135,116 A | 10/2000 | Vogel et al. |
| 6,142,982 A | 11/2000 | Hunt et al. |
| 6,168,800 B1 | 1/2001 | Dobos et al. |
| 6,174,306 B1 | 1/2001 | Fleischmann |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,345,623 B1 | 2/2002 | Heaton et al. |
| 6,398,767 B1 | 6/2002 | Fleischmann |
| 6,458,109 B1 | 10/2002 | Henley et al. |
| 6,488,643 B1 | 12/2002 | Tumey et al. |
| 6,520,982 B1 | 2/2003 | Boynton et al. |
| 6,553,998 B2 | 4/2003 | Heaton et al. |
| 6,557,704 B1 | 5/2003 | Randolph |
| 6,599,262 B1 | 7/2003 | Masini |
| 6,607,495 B1 | 8/2003 | Skalak et al. |
| 6,626,891 B2 | 9/2003 | Ohmstede |
| 6,648,862 B2 | 11/2003 | Watson |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,787,682 B2 | 9/2004 | Gilman |
| 6,794,554 B2 | 9/2004 | Sessions et al. |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,855,860 B2 | 2/2005 | Ruszczak et al. |
| 6,856,821 B2 | 2/2005 | Johnson |
| 6,936,037 B2 | 8/2005 | Bubb et al. |
| 6,942,633 B2 | 9/2005 | Odland |
| 6,942,634 B2 | 9/2005 | Odland |
| 6,951,553 B2 | 10/2005 | Bubb et al. |
| 6,979,324 B2 | 12/2005 | Bybordi et al. |
| 7,022,113 B2 | 4/2006 | Lockwood et al. |
| 7,067,709 B2 | 6/2006 | Murate et al. |
| 7,077,832 B2 | 7/2006 | Fleischmann |
| 7,087,806 B2 | 8/2006 | Scheinberg et al. |
| 7,108,683 B2 | 9/2006 | Zamierowski |
| 7,117,869 B2 | 10/2006 | Heaton et al. |
| 7,128,735 B2 | 10/2006 | Weston |
| 7,195,624 B2 | 3/2007 | Lockwood et al. |
| 7,216,651 B2 | 5/2007 | Argenta et al. |
| 7,361,184 B2 | 4/2008 | Joshi |
| 7,381,859 B2 | 6/2008 | Hunt et al. |
| 7,438,705 B2 | 10/2008 | Karpowicz |
| 7,524,315 B2 | 4/2009 | Blott et al. |
| 7,532,953 B2 | 5/2009 | Vogel |
| 7,534,927 B2 | 5/2009 | Lockwood et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| 7,625,362 B2 | 12/2009 | Boehringer et al. |
| 7,645,253 B2 | 1/2010 | Gura et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,722,582 B2 | 5/2010 | Lina et al. |
| 7,723,560 B2 | 5/2010 | Lockwood et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,811,269 B2 | 10/2010 | Boynton et al. |
| 7,815,616 B2 | 10/2010 | Boehringer et al. |
| 7,837,673 B2 | 11/2010 | Vogel |
| 7,838,717 B2 | 11/2010 | Haggstrom et al. |
| 7,846,141 B2 | 12/2010 | Weston |
| 7,896,864 B2 | 3/2011 | Lockwood et al. |
| 7,909,805 B2 | 3/2011 | Weston |
| 7,910,791 B2 | 3/2011 | Coffey |

(56) References Cited

U.S. PATENT DOCUMENTS

| | | |
|---|---|---|
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,964,766 B2 | 6/2011 | Blott et al. |
| 7,976,519 B2 | 7/2011 | Bubb et al. |
| 8,034,037 B2 | 10/2011 | Adams et al. |
| 8,062,272 B2 | 11/2011 | Weston |
| 8,062,273 B2 | 11/2011 | Weston |
| 8,080,702 B2 | 12/2011 | Blott et al. |
| 8,092,441 B2 | 1/2012 | Sugito |
| 8,118,794 B2 | 2/2012 | Weston |
| 8,152,785 B2 | 4/2012 | Vitaris |
| 8,168,848 B2 | 5/2012 | Lockwood et al. |
| 8,207,392 B2 | 6/2012 | Haggstrom et al. |
| 8,212,100 B2 | 7/2012 | Moore |
| 8,372,049 B2 | 2/2013 | Jaeb et al. |
| 8,372,050 B2 | 2/2013 | Jaeb et al. |
| 8,398,614 B2 | 3/2013 | Blott et al. |
| 8,409,157 B2 | 4/2013 | Haggstrom et al. |
| 8,444,612 B2 | 5/2013 | Patel et al. |
| 8,460,255 B2 | 6/2013 | Joshi et al. |
| 8,529,548 B2 | 9/2013 | Blott et al. |
| 8,535,283 B2 | 9/2013 | Heaton et al. |
| 8,535,296 B2 | 9/2013 | Blott et al. |
| 8,545,464 B2 | 10/2013 | Weston |
| 8,556,871 B2 | 10/2013 | Mormino et al. |
| 8,569,566 B2 | 10/2013 | Blott et al. |
| 8,628,505 B2 | 1/2014 | Weston |
| 8,679,079 B2 | 3/2014 | Heaton et al. |
| 8,795,243 B2 | 8/2014 | Weston |
| 8,829,263 B2 | 9/2014 | Haggstrom et al. |
| 8,834,451 B2 | 9/2014 | Haggstrom et al. |
| 8,864,748 B2 | 10/2014 | Coulthard et al. |
| 8,915,895 B2 | 12/2014 | Jaeb et al. |
| 8,956,336 B2 | 2/2015 | Haggstrom et al. |
| 9,168,330 B2 | 10/2015 | Joshi et al. |
| 9,198,801 B2 | 12/2015 | Weston |
| 9,211,365 B2 | 12/2015 | Weston |
| 9,669,138 B2 | 6/2017 | Joshi et al. |
| 9,795,725 B2 | 10/2017 | Joshi et al. |
| 10,265,445 B2 | 4/2019 | Weston |
| 2001/0031943 A1 | 10/2001 | Urie |
| 2001/0043943 A1 | 11/2001 | Coffey |
| 2002/0065494 A1 | 5/2002 | Lockwood et al. |
| 2002/0115952 A1 | 8/2002 | Johnson et al. |
| 2002/0143286 A1 | 10/2002 | Tumey |
| 2002/0161346 A1 | 10/2002 | Lockwood et al. |
| 2003/0040687 A1 | 2/2003 | Boynton et al. |
| 2003/0078532 A1 | 4/2003 | Ruszczak et al. |
| 2003/0093041 A1 | 5/2003 | Risk, Jr. et al. |
| 2003/0097100 A1 | 5/2003 | Watson |
| 2003/0212357 A1 | 11/2003 | Pace |
| 2003/0212359 A1 | 11/2003 | Butler |
| 2003/0219469 A1 | 11/2003 | Johnson et al. |
| 2004/0006319 A1 | 1/2004 | Lina |
| 2004/0039415 A1 | 2/2004 | Zamierowski |
| 2004/0054338 A1 | 3/2004 | Bybordi |
| 2004/0064111 A1 | 4/2004 | Lockwood et al. |
| 2004/0064132 A1 | 4/2004 | Boehringer et al. |
| 2004/0073151 A1* | 4/2004 | Weston ................. A61F 15/008 602/41 |
| 2004/0076662 A1* | 4/2004 | Riesinger .......... A61F 13/00055 424/445 |
| 2004/0087884 A1 | 5/2004 | Haddock et al. |
| 2004/0093026 A1 | 5/2004 | Weidenhagen et al. |
| 2004/0167482 A1 | 8/2004 | Watson |
| 2004/0193218 A1 | 9/2004 | Butler |
| 2004/0241213 A1 | 12/2004 | Bray |
| 2004/0249353 A1 | 12/2004 | Risk, Jr. et al. |
| 2004/0260230 A1 | 12/2004 | Randolph |
| 2005/0012616 A1 | 1/2005 | Forster et al. |
| 2005/0020955 A1 | 1/2005 | Sanders et al. |
| 2005/0065471 A1 | 3/2005 | Kuntz |
| 2005/0085795 A1 | 4/2005 | Lockwood et al. |
| 2005/0090787 A1 | 4/2005 | Risk, Jr. et al. |
| 2005/0119737 A1 | 6/2005 | Bene et al. |
| 2005/0131327 A1 | 6/2005 | Lockwood et al. |
| 2005/0137539 A1 | 6/2005 | Biggie et al. |
| 2005/0147562 A1 | 7/2005 | Hunter et al. |
| 2005/0177093 A1 | 8/2005 | Barry et al. |
| 2005/0251068 A1 | 11/2005 | Mor |
| 2006/0009744 A1 | 1/2006 | Erdman et al. |
| 2006/0029650 A1 | 2/2006 | Coffey |
| 2006/0107642 A1 | 5/2006 | Smith et al. |
| 2006/0213527 A1 | 9/2006 | Argenta et al. |
| 2006/0259102 A1 | 11/2006 | Slatkine |
| 2007/0055209 A1 | 3/2007 | Patel et al. |
| 2007/0066945 A1 | 3/2007 | Martin |
| 2007/0078366 A1* | 4/2007 | Haggstrom .......... A61F 13/0203 602/53 |
| 2007/0128055 A1 | 6/2007 | Lee |
| 2007/0179460 A1 | 8/2007 | Adahan |
| 2007/0219512 A1 | 9/2007 | Heaton et al. |
| 2007/0225663 A1 | 9/2007 | Watt et al. |
| 2007/0265586 A1 | 11/2007 | Joshi et al. |
| 2008/0051716 A1 | 2/2008 | Stutz |
| 2008/0108977 A1 | 5/2008 | Heaton et al. |
| 2008/0200905 A1 | 8/2008 | Heaton et al. |
| 2008/0306456 A1 | 12/2008 | Riesinger |
| 2009/0012484 A1 | 1/2009 | Nielsen et al. |
| 2009/0069759 A1 | 3/2009 | Blott et al. |
| 2009/0124988 A1 | 5/2009 | Coulthard |
| 2009/0137973 A1 | 5/2009 | Karpowicz et al. |
| 2009/0204085 A1 | 8/2009 | Biggie et al. |
| 2009/0275922 A1 | 11/2009 | Coulthard et al. |
| 2011/0295220 A1 | 12/2011 | Heaton et al. |
| 2012/0041399 A1 | 2/2012 | Blott et al. |
| 2013/0090615 A1 | 4/2013 | Jaeb et al. |
| 2013/0102979 A1 | 4/2013 | Coulthard et al. |
| 2013/0116635 A1 | 5/2013 | Fleischmann |
| 2013/0138054 A1 | 5/2013 | Fleischmann |
| 2013/0150814 A1 | 6/2013 | Buan |
| 2013/0331822 A1 | 12/2013 | Patel |
| 2013/0338614 A1 | 12/2013 | Heaton et al. |
| 2014/0100539 A1 | 4/2014 | Coulthard et al. |
| 2014/0155849 A1 | 6/2014 | Heaton et al. |
| 2014/0188061 A1 | 7/2014 | Locke et al. |
| 2014/0200535 A1 | 7/2014 | Locke et al. |
| 2014/0276490 A1 | 9/2014 | Locke et al. |
| 2014/0276491 A1 | 9/2014 | Luckemeyer et al. |
| 2014/0276497 A1 | 9/2014 | Robinson |
| 2014/0309601 A1 | 10/2014 | Hall et al. |
| 2014/0343519 A1 | 11/2014 | Weston |
| 2015/0065965 A1 | 3/2015 | Haggstrom |
| 2015/0080787 A1 | 3/2015 | Haggstrom et al. |
| 2015/0119829 A1 | 4/2015 | Haggstron et al. |
| 2015/0165101 A1 | 6/2015 | Blott et al. |
| 2015/0173954 A1 | 6/2015 | Blott et al. |
| 2015/0209492 A1 | 7/2015 | Blott et al. |
| 2018/0028729 A1 | 2/2018 | Joshi et al. |

FOREIGN PATENT DOCUMENTS

| | | |
|---|---|---|
| EP | 0 512 543 | 11/1992 |
| EP | 0 853 950 | 7/1998 |
| EP | 1 088 569 | 4/2001 |
| EP | 1 219 311 | 7/2002 |
| EP | 1 476 217 B1 | 3/2008 |
| EP | 2 603 699 | 6/2013 |
| EP | 2079507 | 1/2014 |
| EP | 2 711 034 | 3/2014 |
| EP | 2 305 325 | 4/2014 |
| EP | 2 345 437 | 4/2014 |
| EP | 2 687 245 | 9/2014 |
| EP | 3 072 542 | 9/2016 |
| EP | 3 062 751 | 8/2017 |
| EP | 3 257 486 | 12/2017 |
| FR | 1163907 | 10/1958 |
| FR | 2 939 320 | 6/2010 |
| GB | 2 307 180 A | 11/1996 |
| GB | 2 329 127 A | 3/1999 |
| GB | 2 336 546 A | 10/1999 |
| GB | 2 344 531 A | 6/2000 |

(56) References Cited

FOREIGN PATENT DOCUMENTS

| | | |
|---|---|---|
| GB | 2511523 | 9/2014 |
| JP | H04-354722 | 12/1992 |
| RU | 131622 | 8/2013 |
| WO | WO 1993/009727 | 5/1993 |
| WO | WO 1994/20041 | 9/1994 |
| WO | WO 1996/05873 | 2/1996 |
| WO | WO 2000/21586 | 4/2000 |
| WO | WO 2003/005943 | 1/2003 |
| WO | WO 2003/018098 | 3/2003 |
| WO | WO 2003/030966 | 4/2003 |
| WO | WO 2003/045492 | 6/2003 |
| WO | WO 2003/057070 | 7/2003 |
| WO | WO 2003/057071 | 7/2003 |
| WO | WO 2003/057307 | 7/2003 |
| WO | WO 2003/086232 | 10/2003 |
| WO | WO 2003/092620 | 11/2003 |
| WO | WO 2003/101508 | 12/2003 |
| WO | WO 2004/018020 | 3/2004 |
| WO | WO 2005/009488 | 2/2005 |
| WO | WO 2005/123170 | 12/2005 |
| WO | WO 2006/052839 | 5/2006 |
| WO | WO 2014/113504 | 6/2014 |
| WO | WO 2014/107285 | 9/2014 |
| WO | WO 2014/143488 | 9/2014 |

OTHER PUBLICATIONS

Membrane Filters, in 16 pages, from website: http://www.advantecmfs.com/catalog/filt/membrane.pdf#page=11 (date unknown, but believed to be copyright 2001-2011).

Pentair Pool Products, 2000 Series Stainless Steel D. E. Filters (2006).

International Search Report and Written Opinion, re PCT Application No. PCT/US2006/034824, dated Mar. 20, 2007.

International Preliminary Report on Patentability, re PCT Application No. PCT/US2006/034824, dated Mar. 11, 2008.

International Search Report and Written Opinion, re PCT Application No. PCT/EP2016/059329, dated Jul. 14, 2016.

Nullification of the German part of European patent 2 021 046 (German file references 60 2007 021 330.4), dated Nov. 23, 2015, with translation.

Pentair Pool Products, 2000 Series Stainless Steel D. E. Filters (2006), in 2 pages.

Protz, K., "Moderne Wundauflagen unterstutzen Heilungsprozess", Wundversorgung: Indikation and Anwendung, Geriatrie Journal, Apr. 2005, pp. 3333-3339, with translation, in 17 pages.

\* cited by examiner

WOUND DRESSING WITH VACUUM RESERVOIR

CROSS-REFERENCE TO RELATED APPLICATIONS

This patent application is a continuation application of U.S. patent application Ser. No. 14/585,589, filed on Dec. 30, 2014, which is a continuation application of U.S. patent application Ser. No. 13/775,964, filed on Feb. 25, 2013, which is a continuation application of U.S. patent application Ser. No. 12/686,813, filed on Jan. 13, 2010, which is a divisional application of U.S. patent application Ser. No. 11/516,925, filed on Sep. 6, 2006, which claims the benefit of U.S. Provisional Patent Application No. 60/714,805, filed on Sep. 7, 2005, the entire contents of each are incorporated herein by this reference.

BACKGROUND

1. Technical Field

The present disclosure relates to an apparatus for treating an open wound, and, more specifically, relates to a wound dressing that draws wound fluids into a vacuum reservoir to facilitate the wound healing process.

2. Description of Related Art

Wound closure involves the migration of epithelial and subcutaneous tissue adjacent the wound towards the center of the wound until the wound closes. Unfortunately, closure is difficult with large wounds or wounds that have become infected. In such wounds, a zone of stasis (i.e. an area in which localized swelling of tissue restricts the flow of blood to the tissues) forms near the surface of the wound. Without sufficient blood flow, the epithelial and subcutaneous tissues surrounding the wound not only receive diminished oxygen and nutrients, but, are also less able to successfully fight microbial infection and, thus, are less able to close the wound naturally. Such wounds have presented difficulties to medical personnel for many years.

Wound dressings have been used in the medical industry to protect and/or facilitate healing of open wounds. One popular technique has been to use negative pressure therapy, which is also known as suction or vacuum therapy. A variety of negative pressure devices have been developed to allow excess wound fluids, i.e., exudates to be removed while at the same time isolating the wound to protect the wound and, consequently, reduce recovery time. Various wound dressings have been modified to promote the healing of open wounds.

Issues that continually need to be addressed when using a wound dressing include ease of use, efficiency of healing a wound, and the source of constant or varying negative pressure. Thus, there remains a need to constantly improve negative pressure wound dressings for open wounds.

SUMMARY

In one preferred embodiment, a wound dressing apparatus includes a wound dressing member dimensioned for positioning relative to a wound bed. The wound dressing member includes an internal vacuum reservoir and having a port in communication with the vacuum reservoir for applying subatmospheric pressure to the vacuum reservoir to facilitate removal of fluid from the wound bed. The wound dressing member includes an access door associated therewith and being selectively movable between a closed position substantially enclosing the vacuum reservoir and an open position permitting access to the vacuum reservoir.

The wound dressing member preferably includes a lower absorbent member which is positionable adjacent the wound bed and an upper member. The upper member at least partially defines the vacuum reservoir. The access door is mounted to the upper member. The lower member may comprise a material selected from the group consisting of foams, nonwoven composite fabrics, cellulosic fabrics, super absorbent polymers, hydrogels and combinations thereof. The lower member also may include at least one of a medicament, an anti-infective agent, an antimicrobial, such as polyhexamethylene biguanide (hereinafter, "PHMB"), antibiotics, analgesics, healing factors, vitamins, growth factors, debridement agents and nutrients. The wound dressing member may include an adhesive member which is adapted to be secured about the wound bed to provide a seal between the wound dressing member and tissue surrounding the wound bed.

The wound dressing apparatus may further include a vacuum source in fluid communication with the port. The vacuum source is adapted to supply subatmospheric pressure in a range between about 20 mmHg and about 500 mmHg to the vacuum reservoir. The port may include valve means.

The wound dressing member may include a visual pressure indicator for indicating a level of pressure within the vacuum reservoir. The preferred visual pressure indicator includes color indicia which correspond to a condition of the subatmospheric pressure within the vacuum reservoir. The preferred visual pressure indicator includes a position sensor. The visual pressure indicator may include circuit means and visible alarm means. The circuit means is adapted to actuate the visible alarm means when the position sensor detects a relative positioning of the top member of the wound dressing member to provide a visual indication of the condition of the subatmospheric pressure within the vacuum reservoir.

In another embodiment, a wound dressing apparatus includes a wound dressing member dimensioned for positioning relative to a wound bed. The wound dressing member including an internal vacuum reservoir and has a port in communication with the vacuum reservoir for applying subatmospheric pressure to the vacuum reservoir to facilitate removal of fluid from the wound bed and stimulate wound healing. The wound dressing member includes a visual pressure indicator associated therewith for indicating a level of pressure within the vacuum reservoir. The visual pressure indicator may include color indicia having a plurality of colors corresponding to a condition of the pressure within the vacuum reservoir. The wound dressing member includes a lower absorbent member positionable adjacent the wound bed and an upper member which at least partially defines the vacuum reservoir. At least one of the top member and the lower absorbent member has the visual pressure indicator mounted thereto. The visual pressure indicator may include an electronic position sensor. The visual pressure indicator may further include circuit means and visible alarm means. The circuit means is adapted to actuate the visible alarm means when the position sensor detects a relative positioning of the top member of the wound dressing member to provide a visual indication of the condition of the subatmospheric pressure within the vacuum reservoir.

BRIEF DESCRIPTION OF THE DRAWINGS

Various embodiments of the subject wound dressing are described herein with reference to the drawings wherein.

DESCRIPTION OF THE PREFERRED EMBODIMENTS

The composite wound dressing of the present disclosure promotes healing of a wound via the use of a vacuum reservoir. The vacuum reservoir subjects the wound to vacuum or subatmospheric pressure to effectively draw wound fluid including liquid exudates from the wound bed without the continuous use of a vacuum source or pump. Hence, vacuum pressure can be applied once or in varying intervals depending on the nature and severity of the wound until the composite wound dressing is saturated with exudate or the wound is healed. If the wound dressing is saturated with exudate and the wound is not healed, certain and/or all layers of the composite wound dressing can be replaced and the process of applying subatmospheric pressure can be repeated.

Figure 1:
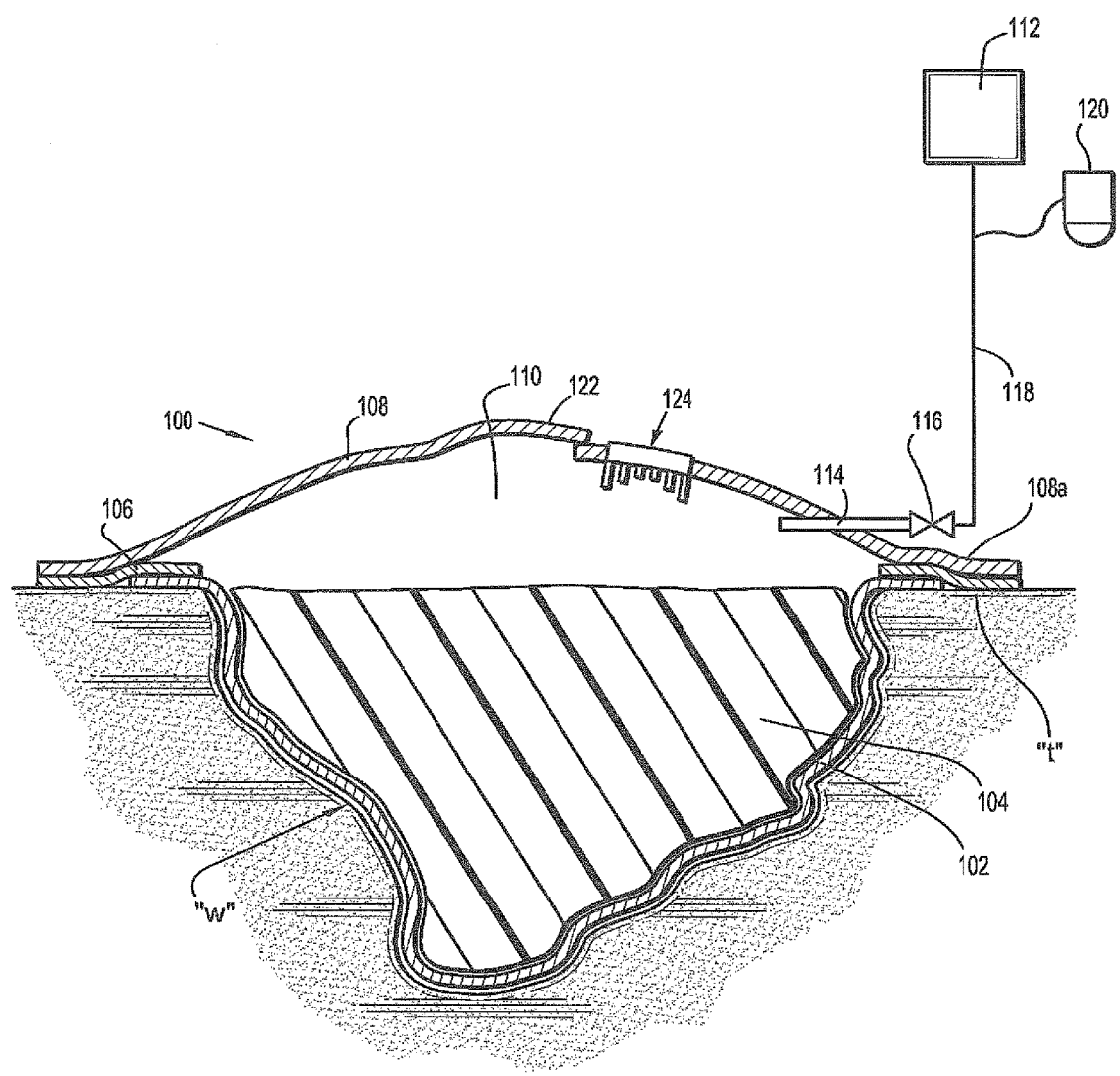
FIG. 1 is a side cross-sectional view of the wound dressing apparatus in accordance with the principles of the present disclosure on a wound bed.
Figure 2:
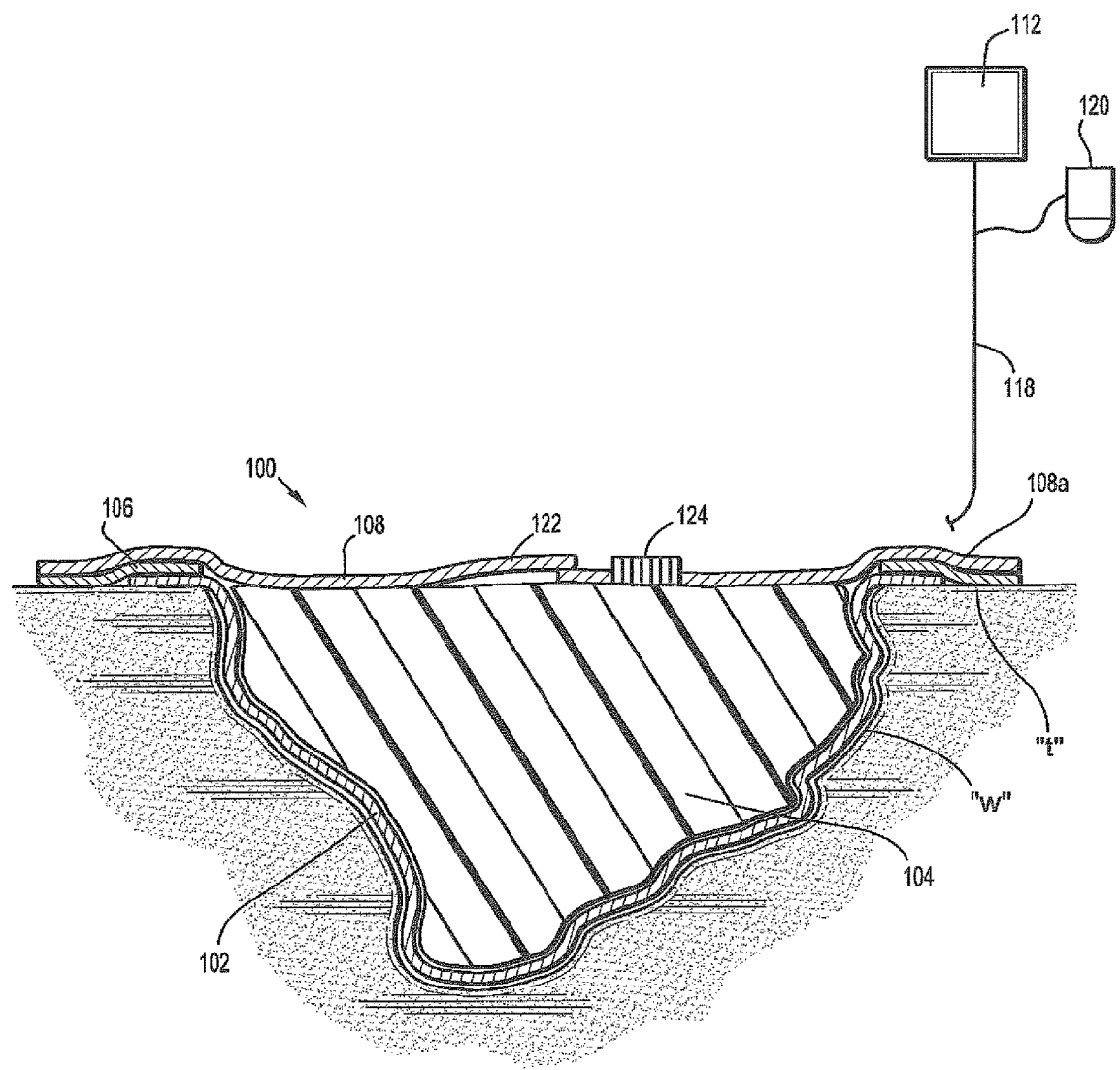
FIG. 2 is a view similar to the view of FIG. 1 illustrating the wound dressing subjected to subatmospheric pressure.
Figure 3:
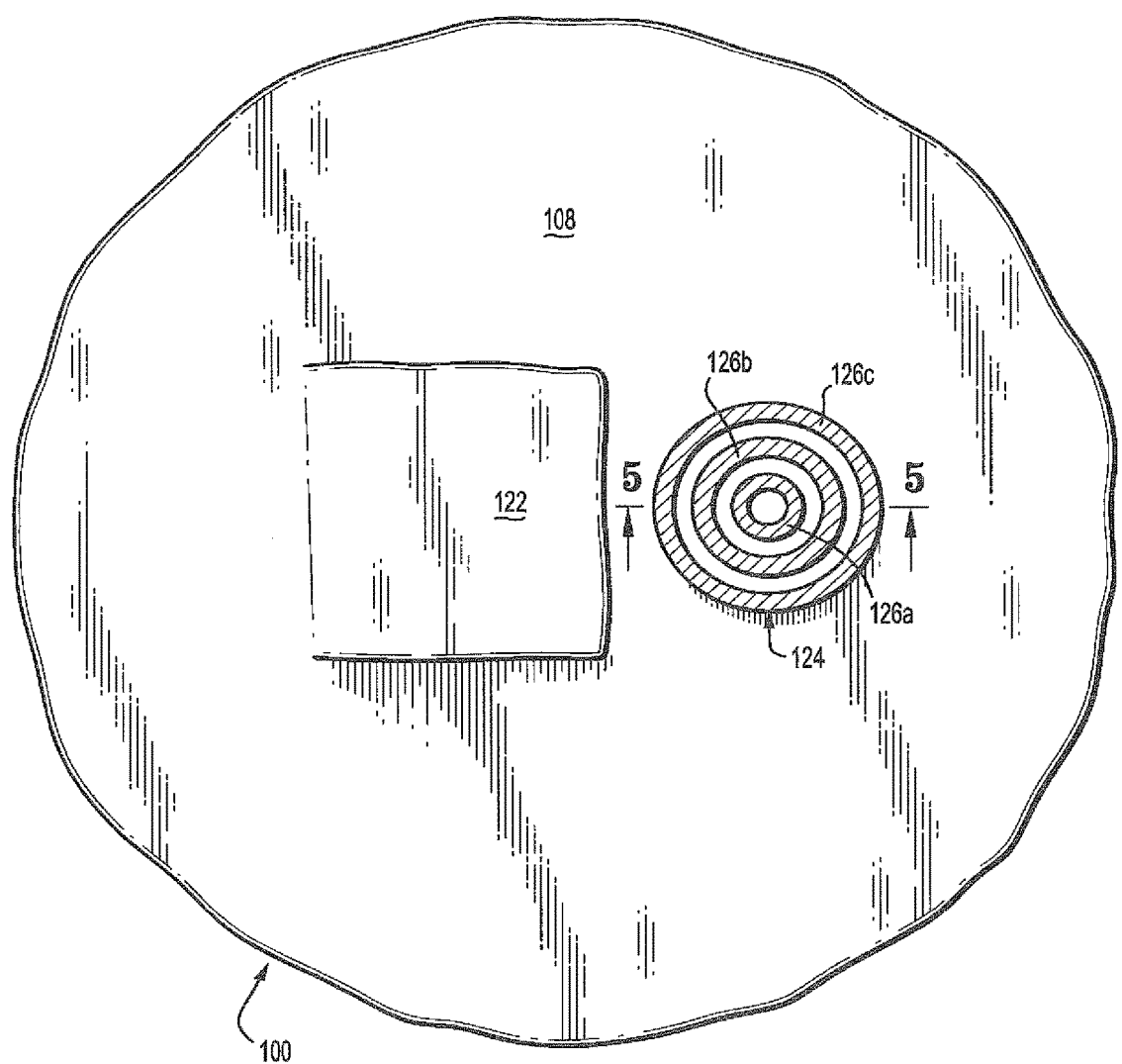
FIG. 3 is a top view of the wound dressing.

Referring now to FIGS. 1-3, the composite wound dressing 100 in accordance with a preferred embodiment of the present disclosure is illustrated in the form of an article with multiple layers arranged in juxtaposed or superposed relation. The multiple layers include, but, are not limited to a lower or base layer 102, an absorbent/packing layer 104, an adherent layer 106, and a top layer 108 which includes and/or defines the internal vacuum reservoir 110.

The base layer 102 is in direct contact with the wound bed "w". The base layer 102 is typically porous allowing passage of subatmospheric pressure to the wound bed. In one preferred embodiment, the base layer includes a "non-adherent" material. "Non-adherent" as used herein refers to a material that does not adhere to tissues in and around the wound bed. "Porous" as used herein refers to a material which contains numerous small perforations or pores which allow wound fluids of all kinds to pass through the material to the dressing layers above. The passage of wound fluid through the porous material may be unidirectional such that wound exudate does not flow back to the wound bed. This direction flow feature could be in the form of directional apertures imparted into the material layer, a lamination of materials of different absorption to the base layer 102 or specific material selection that encourages directional flow. Exemplary materials used as the base layer 102 include a contact layer sold under the trademark XEROFLOW® Kendall Corp., a division of TycoHealthcare. In the alternative, the base layer 102 may include an adherent material.

In addition, agents such as hydrogels and medicaments could be bonded or coated to the base layer 102 to reduce bioburden in the wound, promote healing and reduce pain associated with dressing changes or removal. Medicaments include, for example, antimicrobial agents, growth factors, antibiotics, analgesics, debridement agents and the like. Furthermore, when an analgesic is used, the analgesic could include a mechanism that would allow the release of that agent prior to dressing removal or change. Exemplary triggers of a release mechanism could be temperature change.

The layer proximal to the base layer 102 or composite structures making the base layer 102 is the absorbent/packing layer 104. The absorbent/packing layer 104 of the wound dressing 100 is intended to absorb and capture wound fluid and exudates. Exemplary absorbent materials include foams, nonwoven composite fabrics, hydrogels, cellulosic fabrics, super absorbent polymers, and combinations thereof. Typically, the absorbent/packing layer 104 can absorb up to about 100 cubic centimeters (cc) or more of wound fluid. Preferably, the absorbent material includes the antimicrobial dressing sold under the trademark KERLIX® by Kendall Corp., a division of TycoHealthcare. In one preferred embodiment, the absorbent/packing layer 104 could be preformed or shaped to conform to varying shapes of the wound bed. Those skilled in the art will recognize that the absorbent/packing layer 104 can be formed in any suitable shape. Absorbent/packing layer 104 may include multiple layers. The only requirement as to shape is that the absorbent/packing layer 104 is suitable to treat a particular shape of the wound.

Additionally, the absorbent/packing layer 104 could be treated with medicaments. Medicaments include, for example, an anti-infective agent such as an antiseptic or other suitable antimicrobial or combination of antimicrobials, polyhexamethylene biguanide (hereinafter, "PHMB"), antibiotics, analgesics, healing factors such as vitamins, growth factors, nutrients and the like, as well as a flushing agent such as isotonic saline solution.

With continued reference to FIGS. 1-3, the adherent layer 106 at least encompasses the perimeter of the wound dressing 100 to surround the wound bed to provide a seal around the perimeter of the wound bed "w". For instance, the sealing mechanism may be any adhesive bonded to a layer that surrounds the wound bed "w" or an adhesive applied directly to the skin. The adhesive must provide acceptable adhesion to the tissue "t" surrounding the wound bed "w" skin, e.g., the periwound area, and be acceptable for use on skin without contact deterioration (for example, the adhesive should preferably be non-irritating and non-sensitizing.) The adhesive may be semi-permeable to permit the contacted skin to transmit moisture or may be impermeable. Additionally, the adhesive could be activated or de-activated by an external stimulus such as heat or a given fluid solution or chemical reaction. Adhesives include, for example, the dressing sold under the trademark ULTEC® Hydrocolloid dressing by Kendall Corp., a division of TycoHealthcare.

The adherent layer 106 may also be in the form of an entire layer proximal to the absorbent/packing layer 104 or preferably is annular or "donut shaped" as shown. Preferably, the adherent layer 106 is not bonded to the absorbent/packing layer 104 to allow for easy replacement of the absorbent/packing layer 104. In a preferred embodiment, the adherent layer 106 is at least bonded to the periphery of the base layer 102. In turn, the peripheral portion 108a of the top layer 108 may be bonded to the adherent layer 106 to provide a seal around the perimeter of the wound. Alternatively, the adherent layer 106 may be positioned on the peripheral portion 108a of the top layer 108 and secured to the tissue "t" about the wound bed "w", and not bonded to the base layer 102. As a further alternative, the peripheral portion 108a of the top layer 108 may include an adhesive surface. It is anticipated that removable contact liners may also be used to protect the adhesive surface of the adherent layer 106 prior to use.

The top or upper layer 108 typically seals the top of the wound dressing 100 and helps maintain the appropriate vacuum level within the wound dressing 100. In one preferred embodiment, the top layer 108 includes the flexible transparent dressing manufactured under the trademark POLYSKIN® II by Kendall Corp., a division of TycoHealthcare. POLYSKIN® II is a transparent, semi-permeable material which permits moisture and oxygen exchange with the wound site, and provides a barrier to microbes and fluid containment. In the alternative, the top layer 110 may be impermeable. As a further alternative, the top layer 108 may include a resilient, e.g., elastomeric, material in the shape, e.g., of a dome.

The top layer 108 defines a sealed or enclosed vacuum reservoir 110. The vacuum reservoir 110 is preferably maintained at an appropriate vacuum level for a predetermined period of time sufficient to initiate or complete healing of the wound bed "w", i.e., to draw wound fluid and exudate away from the wound bed "w" while subjecting the wound to subatmospheric pressure. The vacuum may be re-applied as needed to maintain a therapeutic effect. The vacuum may be continuous or intermittent as desired.

As best seen in FIG. 1, the vacuum reservoir 110 is defined within the dome of the top layer 108. As shown in FIG. 2, once vacuum is applied, the dome of the top layer 108 is drawn downwardly toward the absorbent/packing layer 104 with the vacuum or subatmospheric reservoir 110 created beneath the top layer 108. Typically, the top layer 108 includes a vacuum port or connector 114 in fluid communication with the vacuum reservoir 110. Preferably, the vacuum port 114 includes a one-way valve (shown schematically as reference numeral 116) which provides unidirectional flow of suction and may provide a means for allowing connection of the composite wound dressing 100 to the vacuum source 112. The one way valve 116 may be incorporated within the vacuum port 114 or, alternatively, be "in line" with the vacuum source 112. A flexible tubing 118 is connected to the vacuum port 114 and the vacuum source 112. The tubing 118 provides suction to the wound from the vacuum source 112 and enables the wound fluid to be transferred from the wound dressing 100. The tubing 118 may be fabricated from PVC, silicone based material or other flexible materials (polymers). The tubing 118 may optionally include a connection to a collection canister 120 for wound drainage and debris. Hence, the vacuum source 112 can draw wound fluid through the composite wound dressing 100 and tubing 118 into the canister 120. In a preferred embodiment of the present disclosure, the canister 120 is portable so that the patient will have the freedom to move about rather than being confined to a fixed location. The canister 120 may also house an absorbent material to absorb wound fluid and exudate.

The vacuum source 112 may apply vacuum to the wound by means such as a manual pump as disclosed in commonly assigned U.S. Pat. No. 5,549,584 to Gross, the entire contents of which are hereby incorporated herein by reference. In the alternative, the vacuum source 112 may include an automated pump. Typically, the vacuum level is in a range between about 20 mmHg to about 500 mmHg, more preferably, about 40 mmHg and about 125 mmHg. The automated pump may be a wall suction apparatus such as those available in an acute or sub-acute care facility. The automated pump may be in the form of a portable pump. The portable pump may include a small or miniature pump that maintains or draws adequate and therapeutic vacuum levels. In a preferred embodiment, the pump is a portable, lightweight, battery operated, suction pump which attaches to the distal end of the tubing. Typically, the vacuum source 112 has regulation means to apply the optimal vacuum pressure for healing the wound. Furthermore, the vacuum source 112 would preferably contain a mechanism to detect a leak in the system if the optimal vacuum pressure is not achieved. Preferably, the vacuum source 112 would also contain an indicator (not shown) to indicate when the optimal vacuum pressure is achieved. In the alternative, a hand pump in the form of a squeeze bulb or a foot pump may serve as the vacuum source 112.

Preferably, a pump is used as the vacuum source 112. Typical pumps include diaphragm or voice coil activated styles that can deliver variable vacuum up to 50 cc/minute.

Figure 4:
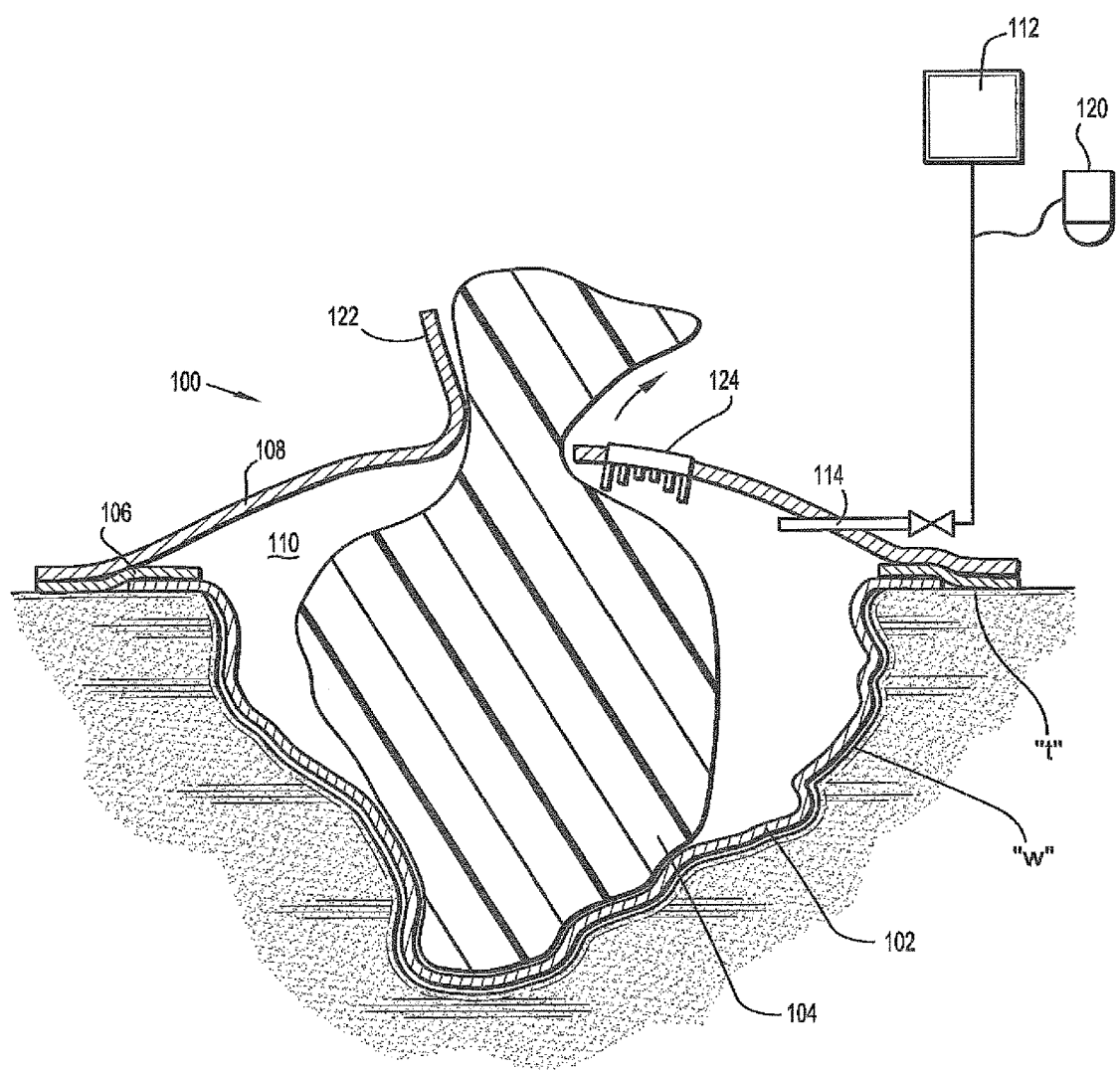
FIG. 4 is a view similar to the view of FIG. 2 illustrating the access door in an open condition to permit access to the internal vacuum reservoir.

With reference now to FIGS. 1-4, the top layer 108 may include an access door 122 to provide access to the interior of the wound dressing 100 and/or the wound bed "w". The door 122 could be a flap integrally formed with the top layer 108 or a separate component connected to the top layer 108 via a hinge or the like. The door 122 is preferably resealable to maintain the integrity of the vacuum reservoir 110 and provide a seal relative to the top layer 108. One suitable means for releasably sealing the door 122 includes a snap fit arrangement, tongue and groove arrangement, "Zip Lock®" arrangement, adhesives, VELCRO®, etc. The door 122 preferably provides access to the wound bed "w" to enable the clinician to monitor the status of the wound, change the absorbent/packing layer 104, or apply additional medical treatment to the wound such as antimicrobial agents, growth factors, debriders, or other wound healing agents as needed. Once the desired procedure is completed, the door 122 would be resealed relative to the top layer 108 to maintain the integrity of the vacuum reservoir 110. FIG. 4 illustrates the removal of the absorbent/packing layer 104 through the door 122 when the door 122 is in an open position. As discussed, a new absorbent/packing layer 104 subsequently may be introduced through the door 122 to absorb the exudates from the wound bed "w".

Figure 5:
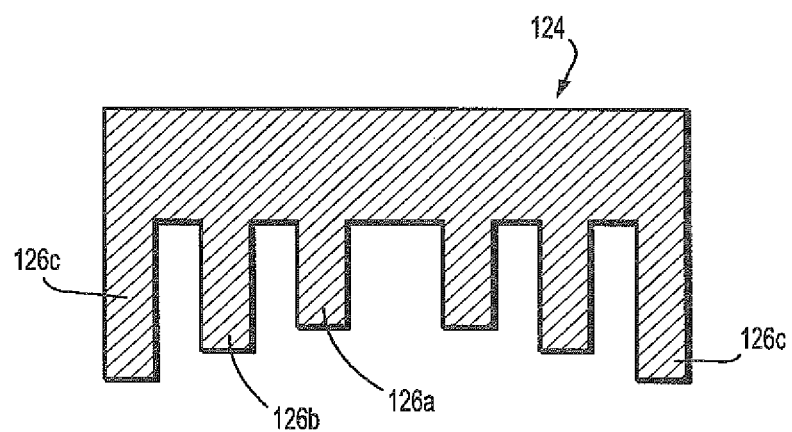
FIG. 5 is a cross-sectional view taken along the lines 5-5 of FIG. 3 illustrating the visual pressure indicator.

With reference now to FIGS. 3 and 5, in conjunction with FIGS. 1-2, the wound dressing 100 may include a visual indicator device 124 mounted to the top layer 108 to provide a visual indication of vacuum pressure within the wound dressing 100. The visual indicator device 124 may include at least one electronic position indicator for detecting the relative position of the top layer 108 and the wound bed, and, thus the state of the vacuum within the wound dressing 100. In accordance with this embodiment, the top layer 108 may have a resilient characteristic either through the material of construction of the top layer 108 or through reinforcement (e.g., elastomeric) members incorporated in the top layer 108.

Figure 6:
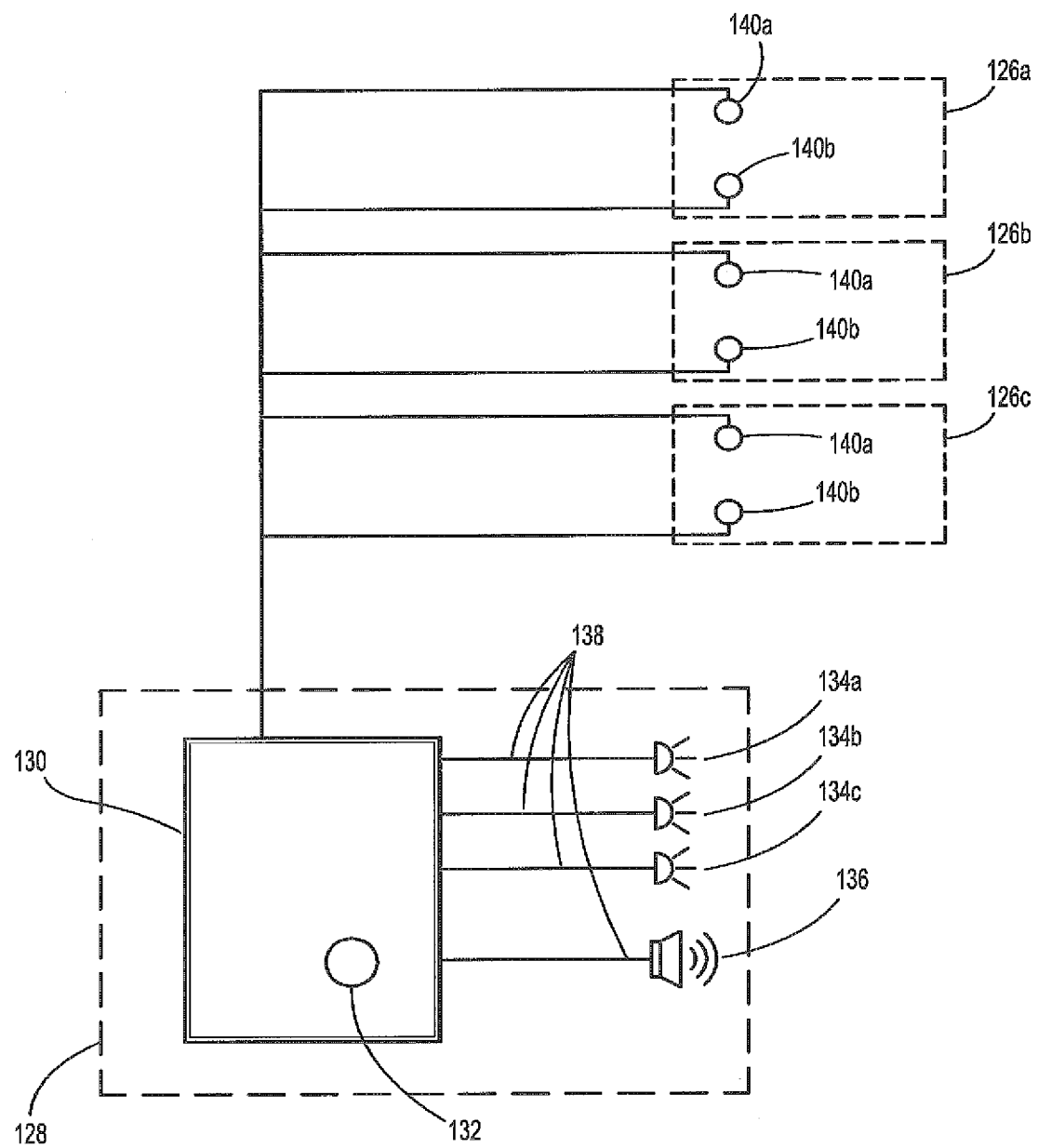
FIG. 6 is a block diagram illustrating the components of the electronic visual indicator device.

In one embodiment depicted in FIG. 6, the visual indicator device 124 includes at least one, preferably, three position-sensitive switches 126a-126c, and a self-powered electronic signaling module 128. The module 128 may include an electronic signaling module circuit board 130, a battery power source 132, at least one transducer including three light emitting diodes (LED) 134a-c and/or a loudspeaker 136 electrically connected 138 to the circuit board 130. The LEDs 134a-c are color coded red, yellow and green respectively. The position-sensitive switches 126a-126c each may be a pressure sensor which electrically bridges contacts 140a, 140b of the visual indicator device 124.

In the embodiment shown, three position switches 126a-c are mounted to top layer 108. The switches 126a-c include switch plates or contact arms arranged as a series of decreasing diameter annular coaxial elements. Alternatively, the switches may be linear in configuration depending downwardly from the top layer 108. The switch plate or contact arm of switches 126a-c are of predetermined length extending downwardly from the top layer 108 within the vacuum reservoir 110. (FIGS. 4 and 5) The contact arm of outer switch 126a of the pressure indicator 124 has the greatest length. The contact arm of the middle switch 126b has a length less than the length of the contact arm of the outer ring 126a. The contact arm of the inner switch 126c has the smallest length. The contacts 140a of switches 126a-c are integrated within the contact arms. Contacts 140b of the switches 126a-c may be disposed on the top surface of the absorbent/packing layer 104 or integrated within the absorbent/packing layer 104 in general longitudinal alignment with their respective contact arms. Alternatively, the position sensor may be a magnetic proximity sensor. The self-powered electronic signaling module 130 may be any conventional modules adapted to emit light and/or audible sound etc. upon closing of the switch.

When the top layer 108 is drawn down by vacuum pressure within the vacuum reservoir 110 toward its vacuum state of FIG. 2, inner switch 126c is in contact with a respective coupler or contact 140b disposed within the absorbent/packing layer 104 thereby energizing the visual indicator device 124 to illuminate the green LED 134c within the pressure indicator device mounted to the top layer 108. The green light of the LEDs 134c indicates a full vacuum condition of the vacuum reservoir 110. As appreciated, switches 126a, 126b may also be in contact with their respective couplers in this vacuum condition of top layer 108. However, it is envisioned that circuit board 130 will incorporate circuitry to override the electrical contact of these two switches when switch 126c is in contact with its respective coupler.

As vacuum pressure decreases and the dome of the top layer 108 begins to assume its normal condition of FIG. 1, through, e.g., the resilient characteristic of the top layer 108 discussed hereinabove, the inner switch 126c loses contact with the absorbent/packing layer 104 while the middle switch 126b maintains/establishes electrical contact with its associated contact 140b. The electrical connection of the middle switch 126b results in illumination of the yellow LED 134b. The yellow LED 134b represents a partial vacuum or marginal vacuum condition of the vacuum reservoir 110. As the vacuum pressure further decreases and the top layer 108 moves towards its fully expanded or normal condition of FIG. 1, the outer switch 126a is the remaining switch in contact with its associated contact 140b within the absorbent/packing layer 104. In this condition, the red LED 134a is energized and visible to the clinician essentially providing a warning that the vacuum within the vacuum reservoir has dissipated or is nearly dissipated (i.e., subatmospheric pressure is close to or no longer present). Consequently, the vacuum source 112 may be actuated either manually or automatically to reestablish the vacuum state within the vacuum reservoir 110. Further vacuum loss will result in the remaining switch 126c losing its contact where no lights are visible to the patient.

It is also envisioned that the circuit board 130 could be devoid of the aforementioned override circuitry. As a result, in the full vacuum condition of dressing 100, each of the green, yellow and red LEDs 134a-134c would be illuminated while in the partial vacuum state, the yellow and red LEDs 134a, 134b would be illuminated and in the warning state, the red LED 134a would be illuminated. It is further envisioned that the loudspeaker 136 could emit an audible alarm when any of the aforementioned vacuum states are realized.

Figure 7:
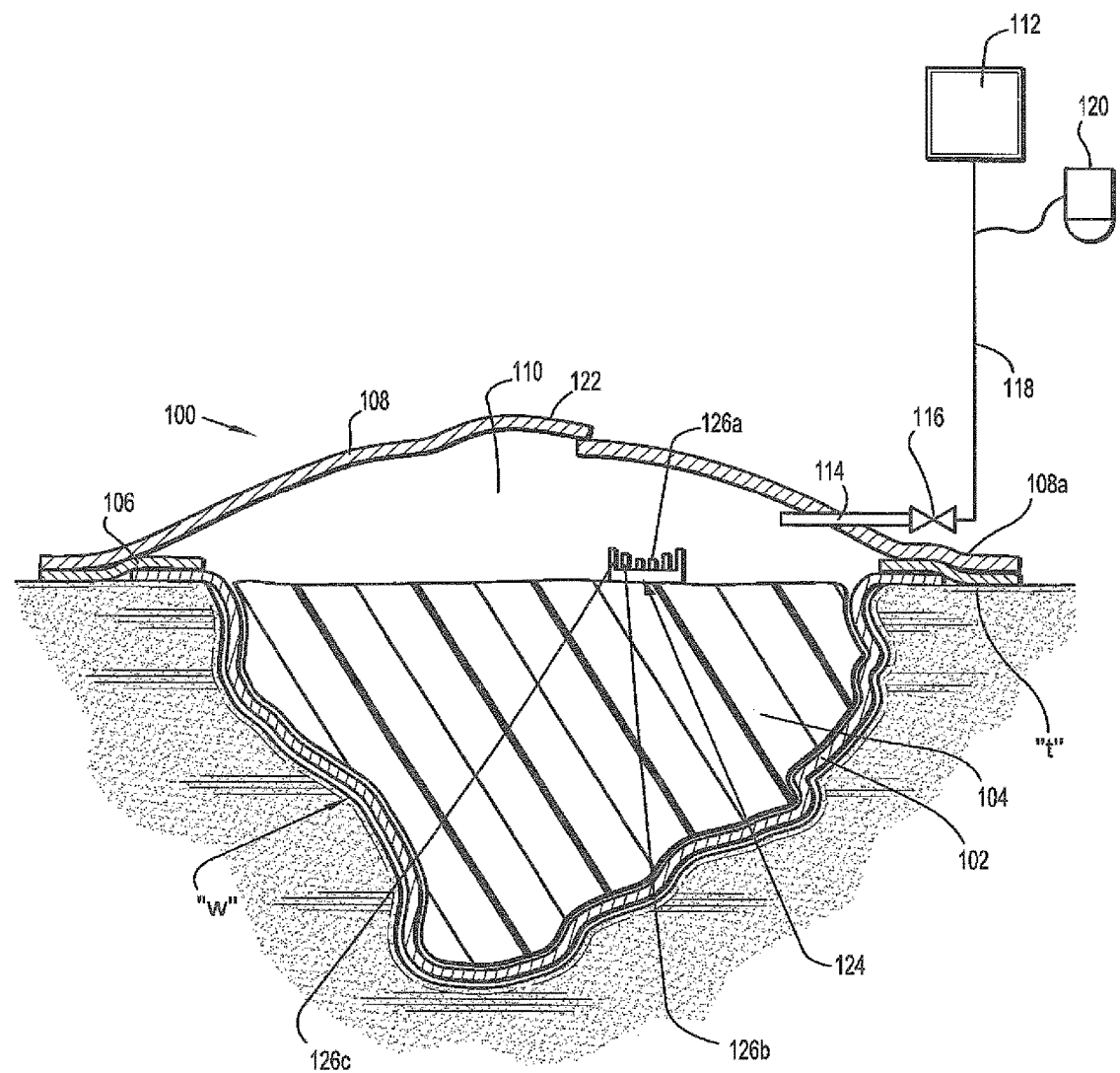
FIG. 7 is a view similar to the view of FIG. 1 illustrating an alternate embodiment of the present disclosure.

FIG. 7 illustrates an alternate embodiment of the visual pressure indicator 124. In accordance with this embodiment, the visual pressure indicator 124 is mounted to the absorbent/packing layer 104 or positioned on the absorbent/packing layer 104 in juxtaposed relation. The top layer 108 is preferably transparent to permit viewing of the pressure indicator 124 through the top layer 108 and into the vacuum reservoir 110. The positioning of the visual pressure indicator 124 is reversed or arranged on its back in a manner where the respective switches 126a-c extend upwardly toward top layer 108. The respective coupler or contacts 140b are incorporated within the top layer 108. In the full vacuum state or condition of FIG. 2, the contact 140b of the top layer 108 is in contact with the switch 126c thereby energizing the LED 134c to display the green color to the clinician. During healing, as the vacuum reservoir begins to lose its vacuum, the top layer 108 moves towards its open condition of FIG. 1, the inner switch 126c loses its contact with its respective coupler 140b of the top layer 108 resulting in electrical contact with the yellow LED 134b indicating a partial vacuum condition of the vacuum reservoir 110. Continued loss of vacuum within the vacuum reservoir 110 causes the electrical contact of the coupler 140b with the outer switch 126c. This contact of the LED 134c with the outer switch 126c is indicated by the presence of its red color and may correspond to a loss or near loss of vacuum within the vacuum reservoir 110 thus prompting the clinician to activate the vacuum source 112 or pursue other clinical measures.

Figure 8:
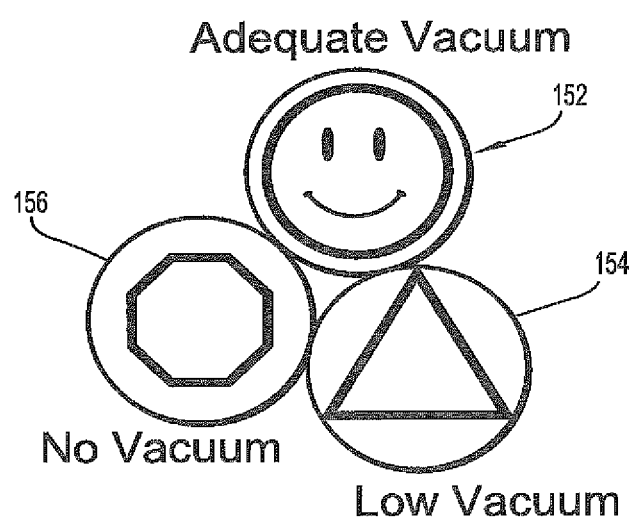
FIG. 8 is a view illustrating an alternate visual indicia arrangement of the visual indicator device.

FIG. 8 illustrates another embodiment where the LEDs 134a-134c are supplemented with additional visual indicia. The visual indicia may include various symbols which correspond to the state of the vacuum within the vacuum reservoir 110. When a desired level of vacuum is reached, the "smiley" symbol 152 would illuminate indicating an adequate vacuum state. A partial vacuum state would result in the illumination of the "caution triangle" symbol 154. A loss or near loss of vacuum would result in the illumination of the "octagon" symbol (no vacuum) 156. One skilled in the art will readily appreciate the design of electronic circuitry to achieve this objective.

Figure 9:
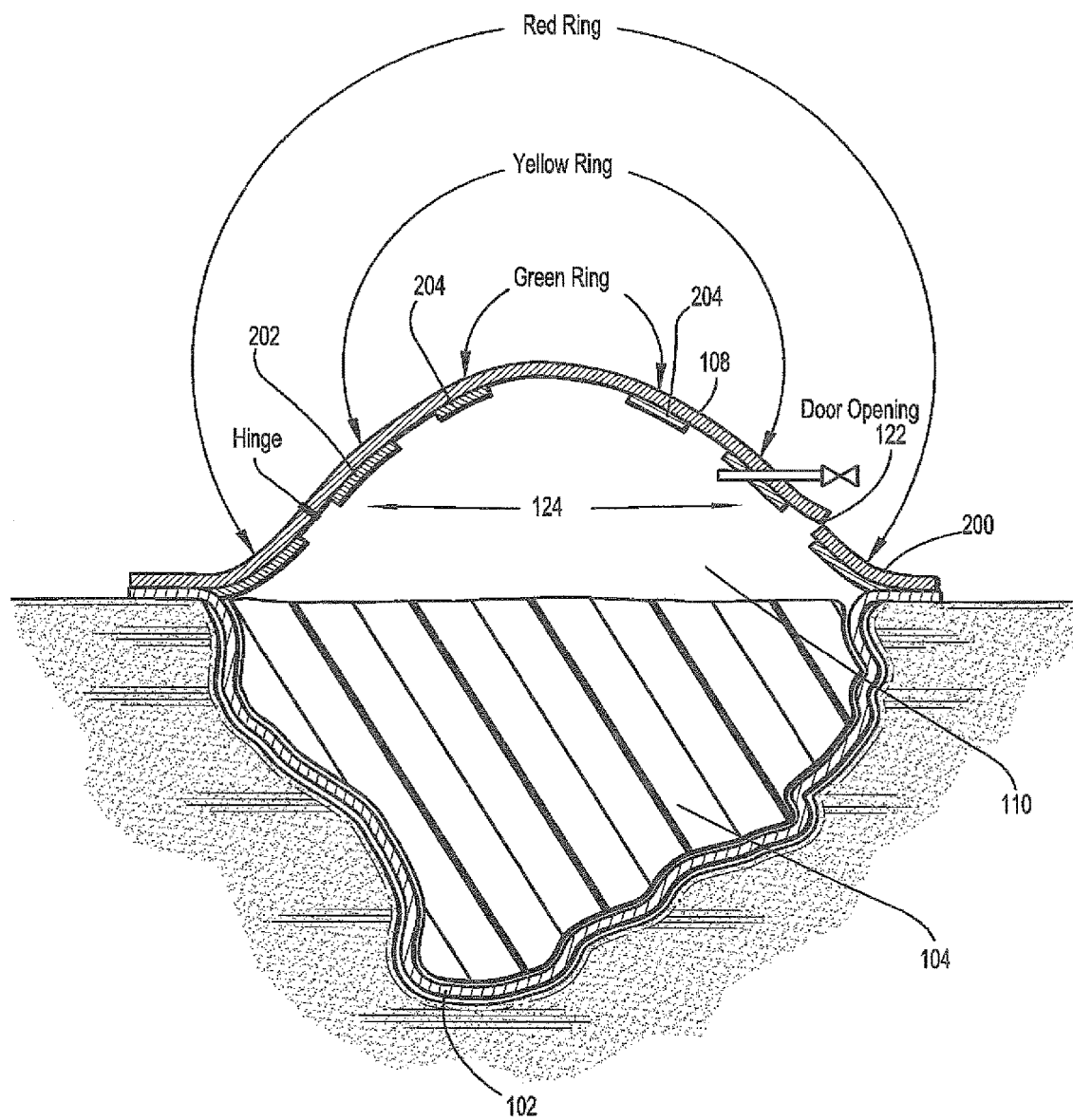
FIG. 9 is a side cross-sectional view of an alternate wound dressing on a wound bed and in the absence of a vacuum.
Figure 10:
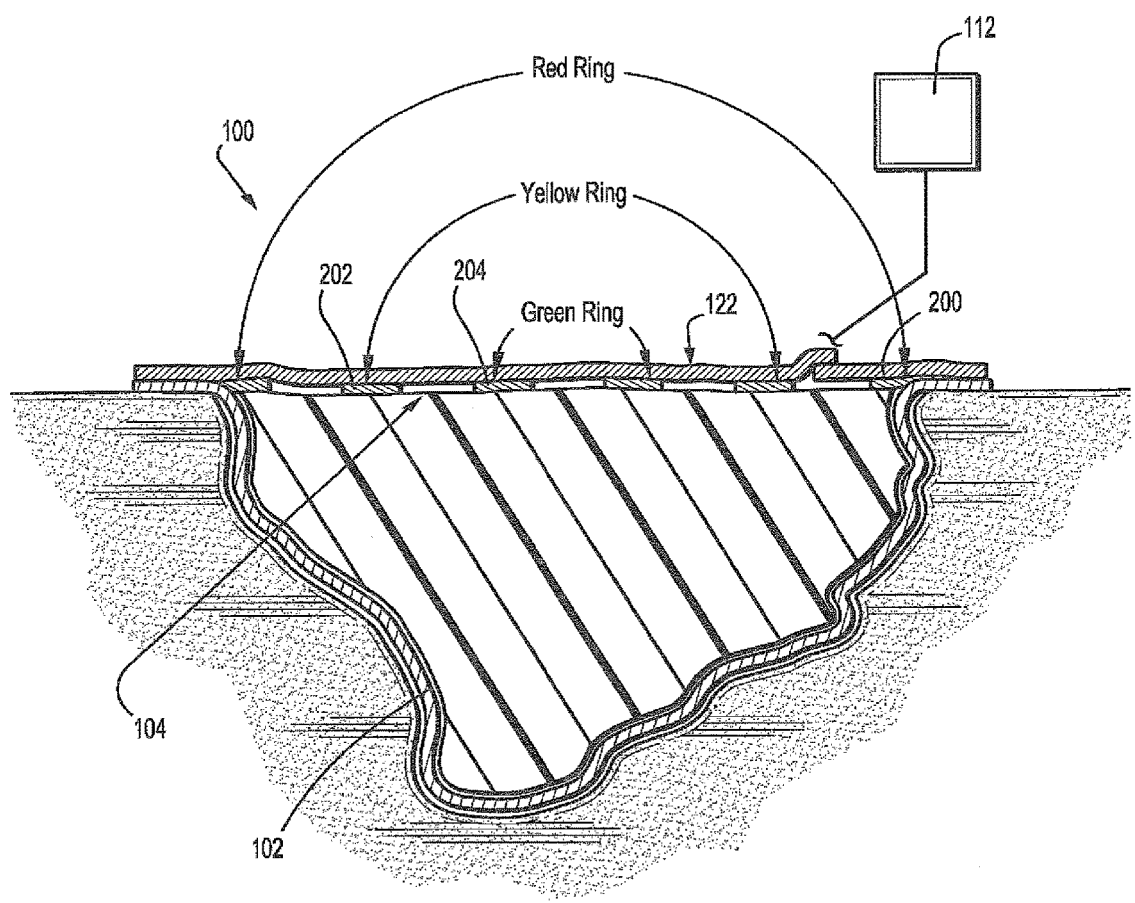
FIG. 10 is a view similar to the view of FIG. 9 illustrating the wound dressing in a contracted condition when subjected to subatmospheric pressure.
Figure 11:
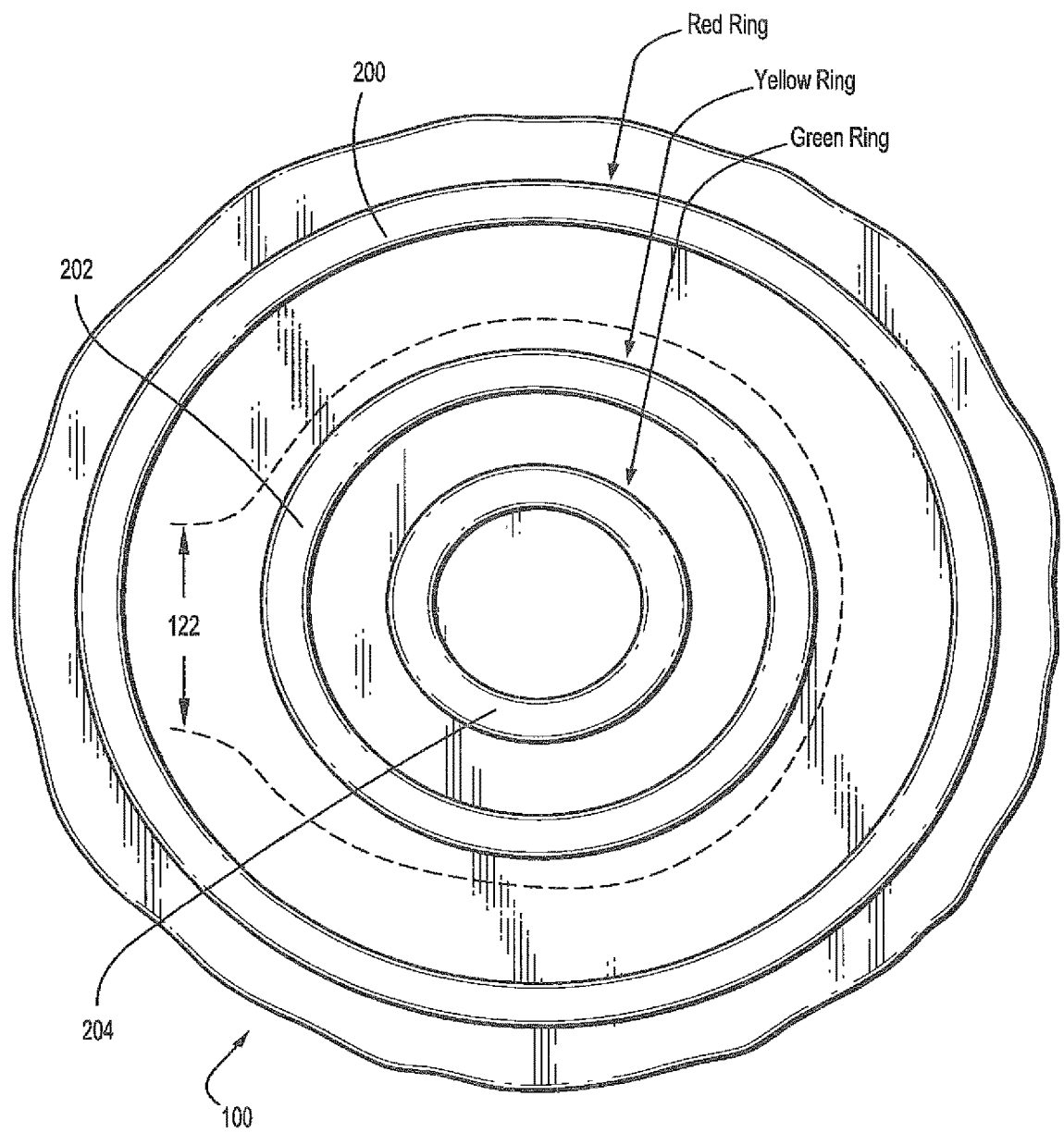
FIG. 11 is a top view of the wound dressing of FIG. 9.

FIGS. 9-11 illustrate an alternate embodiment of the present disclosure. In accordance with this embodiment, the visual indicator device 124 may include a series of rings 200,202,204 disposed on the underside of the top layer 108, e.g., printed on the top layer 108, and arranged in concentric relation as shown. The rings include outer ring 200, middle ring 202 and inner ring 204 and are color coded red, yellow and green, respectively. Each colored ring 200,202,204 is positioned to contact the absorbent/packing layer 104 depending on the state or condition of the vacuum within the vacuum reservoir 110. Under full vacuum depicted in FIG. 10, all the rings 200,202,204 would contact absorbent/packing layer 104 and thus be activated and visible through the top of the wound dressing. As the vacuum within the reservoir dissipates or is reduced, the top layer 110 pulls away from the absorbent/packing layer 104. In one embodiment with an elastomeric dome, the inner ring 204 first loses contact followed by the middle and outer rings, 202, 200, respectively, as the vacuum is reduced. As each colored ring 200,202,204 loses contact with absorbent/packing layer 104, the respective ring becomes less visible or not visible from above the wound dressing 100 thus indicating to the clinician the condition of the vacuum within the vacuum reservoir. The rings 200,202,204 may incorporate electronic switches to be activated in the manner discussed hereinabove in connection with the embodiment of FIGS. 1-6. Alternatively, each ring 200,202,204 may incorporate an analytical test strip device which, e.g., may detect the presence of a predetermined analyte in the exudates contained in the absorbent/packing layer 104. Upon contact with the predetermined analyte, the test strip device of each ring 200,202,204 assumes a color such as red, yellow or green. When a respective ring 200,202,204 loses contact with the predetermined analyte, the color of the respective ring may fade or assume a neutral color. One exampled of a color coded test strip device suitable for use with the present disclosure is disclosed in U.S. Pat. No. 7,049,130 to Carroll et al., issued May 23, 2006, the entire contents of which are incorporated herein by reference. One skilled in the art may determine the parameters and characteristics of a test strip device to perform the objectives discussed hereinabove.

In addition, the door 122 of the embodiment of FIGS. 9-11 is adapted to pivot along hinge 208 to provide access to the vacuum reservoir 110. The opening of the door 122 is disposed adjacent the periphery of the wound dressing 102 and thus provides a relatively large access opening upon pivoting or opening the door 122 along the hinge 208. This facilitates removal and replacement of absorbent/packing layer 104.

It is further contemplated that the wound dressing apparatus may incorporate external means or applications to stimulate tissue growth and/or healing. For example, an ultrasonic transducer may be incorporated into the wound dressing apparatus to impart mechanical energy for the treatment of the tissue such as, for instance, directing thermal or vibratory energy on the wound area to stimulate healing and/or further encouraging exudates removal by vacuum and/or introducing various drugs into the human body through the skin. Other sensor types are also contemplated for incorporation into the wound dressing apparatus including oxygen, chemical, microbial and/or temperature sensors. The detection of oxygen adjacent the wound area would assist the clinician in determining the status of wound healing. The presence of an elevated temperature may be indicative of an infection.

While the disclosure has been illustrated and described, it is not intended to be limited to the details shown, since various modifications and substitutions can be made without departing in any way from the spirit of the present disclosure. For example, it is envisioned the subject matter of the commonly assigned U.S. patent application Ser. No. 11/517,210, filed on Sep. 6, 2006, and which claims priority to U.S. Provisional Application Ser. No. 60/714,812, filed on Sep. 6, 2005, and the subject matter of the commonly assigned U.S. patent application Ser. No. 11/516,216, filed on Sep. 6, 2006, and which claims priority to provisional application No. 60/714,912, filed on Sep. 7, 2005, (the entire contents of each application being incorporated herein) may be incorporated into the present disclosure. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A wound dressing apparatus for use in negative pressure wound therapy, the wound dressing apparatus comprising:
   a wound dressing, the wound dressing comprising:
      a wound contact layer configured to be in direct contact with a wound;
      a wound cover layer configured to be positioned over the wound, wherein the wound cover layer defines an internal vacuum reservoir when the wound cover layer is positioned over the wound; and
      an absorbent layer positioned between the wound contact layer and the wound cover layer; and
   a visual indicator configured to indicate a condition of the wound dressing, wherein the visual indicator comprises one or more light emitting sources positioned within a periphery of the wound cover layer of the wound dressing.

2. The wound dressing apparatus according to claim 1, wherein the visual indicator comprises a color indicator.

3. The wound dressing apparatus according to claim 1, further comprising a vacuum pump configured to provide negative pressure to the reservoir.

4. The wound dressing apparatus according to claim 3, wherein the vacuum pump is configured to be positioned external to the wound cover layer.

5. The wound dressing apparatus according to claim 3, wherein the vacuum pump comprises a manual pump.

6. The wound dressing apparatus according to claim 3, wherein the vacuum pump comprises a compressible suction device.

7. The wound dressing apparatus according to claim 3, wherein the vacuum pump comprises an automated pump.

8. The wound dressing apparatus according to claim 1, further comprising an adhesive material on an underside of the wound cover layer to contact tissue surrounding the wound.

9. The wound dressing apparatus according to claim 8, wherein the adhesive material comprises an annular layer positioned on a peripheral portion of the wound cover layer.

10. The wound dressing apparatus according to claim 1, wherein the absorbent layer comprises a super absorbent polymer and a fibrous material.

11. The wound dressing apparatus according to claim 10, wherein the fibrous material comprises cellulose.

12. The wound dressing apparatus according to claim 1, further comprising a vacuum port on the wound cover layer in fluid communication with the internal vacuum reservoir.

13. The wound dressing apparatus according to claim 12, further comprising a flexible tubing configured to connect the vacuum port to a vacuum pump.

14. The wound dressing apparatus according to claim 1, wherein the visual indicator is configured to indicate a condition within the vacuum reservoir associated with a negative pressure level or a leak in the wound dressing.

15. The wound dressing apparatus according to claim 1, further comprising an electronic signaling module circuit board and a battery power source in electrical communication with the visual indicator.

16. The wound dressing apparatus according to claim 1, wherein the wound cover layer is transparent, and the visual indicator is configured to be viewed through the transparent wound cover layer.

17. The wound dressing apparatus according to claim 1, wherein the visual indicator comprises a plurality of different visual indicia.

18. The wound dressing apparatus according to claim 1, wherein the visual indicator comprises a plurality of light emitting sources for different conditions.

19. The wound dressing apparatus according to claim 2, wherein the visual indicator comprises a plurality of light emitting sources of different colors.

* * * * *